(12) United States Patent
Zhi et al.

(10) Patent No.: US 12,381,004 B2
(45) Date of Patent: Aug. 5, 2025

(54) SYSTEMS AND METHODS FOR PREDICTING HEALTH OUTCOMES

(71) Applicant: Aetna Inc., Hartford, CT (US)

(72) Inventors: Naiqian Zhi, Hartford, CT (US); Sarah Wohlman, Hartford, CT (US); Alex Xu, Hartford, CT (US); Ryan Berns, Hartford, CT (US); Rajiv Bhan, Hartford, CT (US)

(73) Assignee: Aetna Inc., Hartford, CT (US)

( * ) Notice: Subject to any disclaimer, the term of this patent is extended or adjusted under 35 U.S.C. 154(b) by 724 days.

(21) Appl. No.: 17/703,901

(22) Filed: Mar. 24, 2022

(65) Prior Publication Data

US 2023/0307127 A1    Sep. 28, 2023

(51) Int. Cl.
*G16H 50/20* (2018.01)
*G06F 40/40* (2020.01)
(Continued)

(52) U.S. Cl.
CPC ............ *G16H 50/20* (2018.01); *G06F 40/40* (2020.01); *G16H 10/60* (2018.01); *G16H 40/20* (2018.01); *G16H 40/67* (2018.01); *G16H 50/30* (2018.01)

(58) Field of Classification Search
CPC ........ G16H 50/20; G16H 10/60; G16H 40/20; G16H 40/67; G16H 50/30; G06F 40/40; G06F 40/20
See application file for complete search history.

(56) References Cited

U.S. PATENT DOCUMENTS 11,504,029 B1 * 11/2022 Martin ................. H04W 4/027
2017/0132395 A1    5/2017 Futch
(Continued)

FOREIGN PATENT DOCUMENTS

AU    2021104281 A4 *  5/2022

OTHER PUBLICATIONS

Bellos, Christos; Papadopoulos, Athanasios; Fotiadis, Dimitrios; Rosso, Roberto. Annual International Conference of the IEEE Engineering in Medicine and Biology Society. IEEE Engineering in Medicine and Biology Society. Annual International Conference 2010: 2890-3. (2010) (Year: 2010).*

(Continued)

*Primary Examiner* — Linh Giang Le
(74) *Attorney, Agent, or Firm* — Leydig, Voit & Mayer, Ltd.

(57) ABSTRACT

A system and method are disclosed for predicting short term health outcomes based on data collected by a wearable device such as an activity tracker or a smart watch. Artificial Intelligence (AI) algorithms are configured to process an input vector that includes monitored parameter data collected by the wearable device as well as embedding data obtained from health records corresponding to a user account registered to the wearable device. In particular, a framework is defined that includes a random forest model configured to classify a user based on the monitored parameter data and embedding data. Based on a positive health outcome classification, a minimum value is assigned to a health index value for the user or, based on a negative health outcome classification, a gradient boosting machine is configured to generate the health index value. Various operations can be performed based on the assigned health index value for the user.

20 Claims, 7 Drawing Sheets

(51) Int. Cl.
   *G16H 10/60*   (2018.01)
   *G16H 40/20*   (2018.01)
   *G16H 40/67*   (2018.01)
   *G16H 50/30*   (2018.01)

(56) References Cited

U.S. PATENT DOCUMENTS

| | | |
|---|---|---|
| 2018/0232495 A1 | 8/2018 | Li et al. |
| 2020/0075152 A1 | 3/2020 | Radovcic |
| 2020/0138360 A1 | 5/2020 | Fan et al. |
| 2020/0202997 A1 | 6/2020 | Hadad et al. |

OTHER PUBLICATIONS

Mikolov et al., "Efficient Estimation of Word Representations in Vector Space," ICLR Workshop Papers (2013).

* cited by examiner

SYSTEMS AND METHODS FOR PREDICTING HEALTH OUTCOMES

TECHNICAL FIELD

The application relates to a model for predicting health outcomes for one or more individuals. More specifically, the application is directed to artificial intelligence algorithms configured to analyze wearable activity tracker data and additional embedding data to assist with prediction of future health outcomes.

BACKGROUND

Wearable health monitoring systems such as the features built into consumer devices like a Fitbit® device or an Apple® Watch, among others, or clinical devices like network connected blood glucose monitors are becoming more common. Consumers are tracking their steps (e.g., pedometer), heart rate (e.g., resting hear rate, peak heart rate, heart rate variability, etc.), oxygen level (e.g., VO2 Max), activity levels (e.g., calories, minutes of exercise, etc.), and the like using these devices, typically to encourage a more active and healthy lifestyle. This data generates thousands or millions of data points for a consumer, and some of this information can be highly correlated to the presence of certain diseases, oftentimes undiagnosed. However, this data is typically not shared with a patient's primary care physician or used in any clinical setting for medical diagnosis.

Some of the consumer companies have developed application programming interfaces (APIs) that allow this data to be shared with third parties, such as a clinician or a company offering health-based incentives such as discounts for those individuals that meet certain goals. In some cases, certain parameters like heart rate or VO2 max can be tracked over time and analyzed by artificial intelligence algorithms to attempt to detect certain health conditions. However, such algorithms are typically limited as they are not tailored to a specific user's physiology. The effectiveness of the artificial intelligence algorithm might not be sufficient for a user to rely on the output of said algorithm. Therefore, there is a need to improve the algorithms directed to use this wearable activity tracker data.

SUMMARY

A system and method for utilizing wearable device data to perform health monitoring are disclosed. Deep learning and/or Machine Learning techniques are utilized to analyze monitored parameter data collected by a wearable device in conjunction with additional embedding data derived from health records or other sources. In particular, the techniques and systems described herein can be utilized by insurance providers or other sources of health record information to supplement the monitored parameter data collected by the wearable device.

In accordance with a first aspect of the present disclosure, a system for predicting health outcomes is disclosed. The system includes a memory storing instructions and one or more processors. The one or more processors, responsive to executing the instructions, are configured to: receive monitored parameter data from a wearable device; obtain embedding data corresponding to a user registered to the wearable device; process the monitored parameter data and the embedding data by a random forest model to generate a classification of the user; responsive to the user being classified according to a first classification, process the monitored parameter data and the embedding data by a gradient boosting machine (GBM) model to generate an index value, or responsive to the user being classified according to a second classification, assign the index value a minimum index value; and perform an operation based on the index value.

In some examples of the first aspect, the wearable device is an activity tracker. The monitored parameter data includes data points related to one or more of: a heart rate; an oxygen level; an activity level including at least one of a number of steps, a number of flights climbed, or a duration of exercise; or a number of calories burned.

In some examples of the first aspect, the monitored parameter data further includes information logged by a user manually.

In some examples of the first aspect, obtaining the embedding data comprises processing health records for a user via a natural language processing algorithm. The health records correspond to the user registered to the wearable device.

In some examples of the first aspect, the health records are stored in a database and comprise at least one of: claims records received from a health care provider; prescription records received from a pharmacy; or laboratory results received from a laboratory or other health care provider.

In some examples of the first aspect, the operation comprises sending a notification message to at least one of the wearable device or a client device associated with the wearable device.

In some examples of the first aspect, the notification message is transmitted responsive to determining that the index value is above a threshold value to provide the user of the wearable device with a suggested action.

In some examples of the first aspect, the suggested action includes information to facilitate scheduling an appointment with a healthcare provider.

In some examples of the first aspect, the operation comprises generating an invoice for the user. The invoice may be adjusted based on the index value.

In some examples of the first aspect, the operation comprises dividing a plurality of users similar to the user into at least two groups. A similarity of the users is determined based on the index value for each user in the plurality of users. The operation further comprises taking a first action with respect to a first group of users in the at least two groups and taking a second action, different from the first action, with respect to a second group of users in the at least two groups.

In accordance with a second aspect of the present disclosure, a method for predicting health outcomes is disclosed. The method includes the steps of: receiving monitored parameter data from a wearable device; obtaining embedding data corresponding to a user registered to the wearable device; processing the monitored parameter data and the embedding data by a random forest model to generate a classification of the user; responsive to the user being classified according to a first classification, processing the monitored parameter data and the embedding data by a gradient boosting machine (GBM) model to generate an index value, or responsive to the user being classified according to a second classification, assign the index value a minimum index value; and performing an operation based on the index value.

In some examples of the second aspect, the wearable device is an activity tracker. The monitored parameter data includes data points related to one or more of: a heart rate; an oxygen level; an activity level including at least one of a number of steps, a number of flights climbed, or a duration of exercise; or a number of calories burned.

In some examples of the second aspect, the monitored parameter data further includes information logged by a user manually.

In some examples of the second aspect, obtaining the embedding data comprises processing health records for a user via a natural language processing algorithm. The health records correspond to the user registered to the wearable device.

In some examples of the second aspect, the health records are stored in a database and comprise at least one of: claims records received from a health care provider; prescription records received from a pharmacy; or laboratory results received from a laboratory or other health care provider.

In some examples of the second aspect, the operation comprises sending a notification message to at least one of the wearable device or a client device associated with the wearable device.

In some examples of the second aspect, the notification message is transmitted responsive to determining that the index value is above a threshold value to provide the user of the wearable device with a suggested action.

In some examples of the second aspect, the suggested action includes information to facilitate scheduling an appointment with a healthcare provider.

In some examples of the second aspect, the operation comprises generating an invoice for the user. The invoice may be adjusted based on the index value.

In some examples of the second aspect, the operation comprises dividing a plurality of users similar to the user into at least two groups. A similarity of the users is determined based on the index value for each user in the plurality of users. The operation further comprises taking a first action with respect to a first group of users in the at least two groups and taking a second action, different from the first action, with respect to a second group of users in the at least two groups.

In accordance with a third aspect of the present disclosure, a non-transitory computer readable medium is provided. The computer readable medium stores instructions that, responsive to execution by one or more processors, cause the one or more processors to perform a method according to any of the examples of the second aspect.

DETAILED DESCRIPTION

Artificial Intelligence (AI) and Machine Learning (ML), including Deep Learning Neural Networks (DLNN) or other ML algorithms, can be utilized to assist in predicting a health index associated with various individuals (i.e., users). A wearable device, such as a wearable activity tracker, oximeter, blood glucose monitor, or the like, can provide one or more monitored parameters to a server device. The monitored parameters can include, but are not limited to, a heart rate, heart rate variability, an electro cardiogram (ECG), a blood oxygen level, a duration of exercise, a number of steps, an altitude, exposure to environmental parameters (e.g., audio signals, air quality, temperature, etc.), menstruation cycles (e.g., basal body temperature, etc.), sleep cycles, acceleration (e.g., fall detection), and the like. The parameters can be logged automatically via sensor input or manually via user input, or any combination thereof. In some examples, the wearable device can be paired with other devices (e.g., blood glucose monitor, etc.) to collect parameter data. The monitored parameters can provide data points collected periodically, such as every second, minute, hour, or day. Different parameters can be collected at different frequencies. For example, a heart rate may be collected every minute whereas a heart rate variability can be collected daily (e.g., as derived from a plurality of heart rate data points collected throughout a 24 hour period).

A user registers the wearable device with a user account. The user account can be associated with additional data that can be used to supplement the monitored parameter data from the wearable device. For example, the additional data can include claims data for an insured person that is maintained by an insurance provider, which can include data collected from the insured person's primary care physician, clinical labs, pharmacies, or other health providers that submit claims information to the insurance provider for payment and/or processing. The claims data provides the insurance provider with additional insight into the health history of the patient that is useful for augmenting an artificial intelligence algorithm tasked with analyzing the information from the wearable device.

While the wearable device provides the AI algorithm with limited health information in a real-time or near real-time basis, the data is typically limited in scope and only provides insight into a small number of parameters related to a user's health. In contrast, the claims information may provide much more detailed insight into a specific user's physiology, but is typically collected on a much more limited basis (e.g., during once or twice a year appointments, when a person fills a prescription, when labs are run, etc.). By combining this data to provide a broad range of information to an AI algorithm, much more accurate assessments can be made by the AI algorithm. Experimental tests have seen 5-10% increases in accuracy of AI algorithms trained based on both monitored parameter data from a wearable device as well as additional embedding data from health records.

However, the number of users that collect data via wearable activity trackers can be limited. For example, not everyone owns a wearable activity tracker as the cost of these devices can sometimes be quite high. This can limit the use of such data to a small subset of individuals in a much larger group. Further, available claims data may be limited in certain situations such as when an individual is only a potential member of an insurance plan provided by an insurance provider or when an individual has been relatively healthy and does not use many health services. In such cases, it would be beneficial to be able to accurately impute the characteristics of a specific subset of individuals for which such data is available to other subsets of individuals that may be associated with a sparse data set.

In some examples, a framework can be defined that is configured to analyze available data to predict a health index for a user. In an example, the health index indicates a likelihood that health expenditures by that user will exceed a threshold within a given timeframe, such as the next 90 days. The health index values can be used in a variety of ways that can be particularly useful. For example, a health index can be used to drive engagement with particular members to engage in incentive or intervention programs, such as subsidized gym memberships, rebates for reaching monthly health goals, and the like. Notifications can be sent to members in response to the members' health index values in order to drive this engagement. In other cases, a health index value can be used to encourage a user to seek health services prior to experiencing an acute event. For example, a health plan member can be encouraged to schedule a yearly physical to attempt to catch any health issue before the issue progresses to an emergency health event, and a timing of the notification can be driven by an increase in the user's health index value (i.e., when the health index value exceeds a threshold value, a notification is sent to the user).

Given the large number of insured individuals that may be members of a particular health insurance product, and a limited number of resources the insurance provider can deploy to decrease costs related to providing healthcare to those individuals, the AI algorithms can help identify those individuals likely to be the main sources of health related costs in the near-term, and then target those limited resources in an effort to contact only that subset of the total population for which intervention is likely to be effective. Other processes that make use of the health index value are within the scope of the present disclosure, some of which are discussed in more detail below.

Figure 1A:
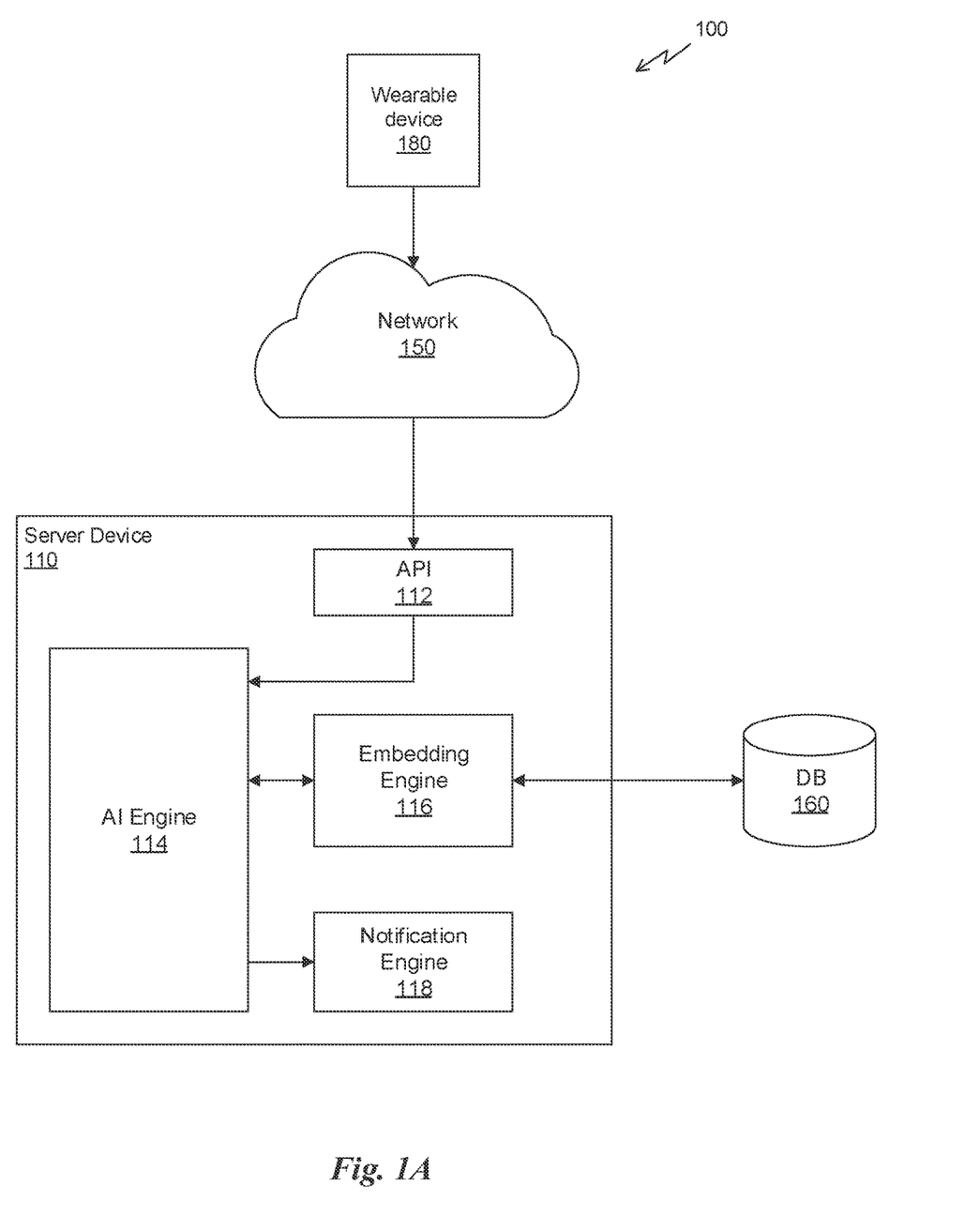
FIG. 1A illustrates a system for monitoring health conditions, in accordance with some examples.

FIG. 1A illustrates a system 100 for predicting health outcomes, in accordance with some examples. As depicted in FIG. 1A, the system 100 includes a server device 110 connected to a network 150. The server device 110 comprises a memory and one or more processors configured to execute instructions. In an example, the server device 110 is a blade server included in a chassis on a rack of a data center. In another example, the server device 110 is a virtual machine that is run in the cloud. Although the components shown in the server device 110 can be executed by a single processor, in other examples, the server device 110 can refer to two or more server devices, each component included in the server device 110 executed by a particular one or more of the two or more server devices. For example, in an example, the AI engine 114 can be executed on a second server device that is implemented in a public cloud such as Amazon® Web Services or Microsoft® Azure. The API 112, embedding engine 116, and/or notification engine 118 can be implemented on a private server device hosted in a data center operated by an insurance provider and can be configured to communicate with the AI engine 114 over a network. It will be understood that reference to a single server device 110 can include reference to multiple server devices.

In some examples, the server device 110 includes an application programming interface (API) 112, an artificial intelligence (AI) engine 114, an embedding engine 116, and a notification engine 118. The API 112 implements a set of algorithms to process API calls from a client. In an example, the API 112 is configured to receive data packets that include the API calls from a wearable device 180. The API calls can include monitored parameter data collected by the wearable device 180. As used herein, the term "monitored parameter data" refers to one or more data points (e.g., samples) of each of one or more monitored parameters such as, but not limited to, a heart rate, heart rate variability, and ECG, an oxygen level, an activity level including at least one of a number of steps, a number of flights climbed, or a duration of exercise, a number of calories burned, a basal body temperature, a sleep duration, a blood glucose level, or the like. For example, the wearable device 180 can include light sensors that, when placed proximate a user's skin, are used to monitor a user's heart rate or blood oxygen level. As another example, the wearable device 180 can include a temperature sensor placed proximate the user's skin, that measures a surface temperature of the user's body at the location of the temperature sensor. The wearable device 180 collects one or more data points over a period of time such as a day or week, and then the wearable device 180 generates an API call including the data points and transmits the API call to the server device 110 via the network 150.

In some examples, the network 150 is a wide area network (WAN) such as the Internet. In other examples, the network 150 can be a radio access network such as a $4^{th}$ Generation (LTE, 4G) or Next Generation (5G) cellular network. In yet other examples, the network 150 can be a local area network (LAN) or a personal area network (PAN). The data packets can be Internet Protocol (IP) packets. It will be appreciated that any network, wired or wireless, can be utilized to transmit monitored parameter data to the server device 110 using any technically feasible protocols.

In some examples, the API 112 pre-processes the monitored parameter data received from the wearable device 180 and transmits the processed monitored parameter data to the AI engine 114. For example, the heart rate data can represent a number of data points, and the API 112 can be configured to derive average daily heart rate data from the monitored parameter data. In an example, the API 112 can be configured to filter the monitored parameter data to select only a subset of parameters that are applicable for a given AI algorithm. For example, the monitored parameter data can include heart rate data, step information, calorie information, and oxygen level information. A particular AI algorithm may only call for heart rate data and oxygen level information and, therefore, the API 112 is configured to discard the step information and calorie information.

In some examples, the API 112 is configured to anonymize the monitored parameter data. Information related to a user's health is a privacy concern and, therefore, the API 112 can take steps to ensure any personally identifying information (PH) is removed before the monitored parameter data is forwarded to the AI engine 114. It will be appreciated that the API 112 may need to associate the monitored parameter data with a particular user or device, such as by using an identifier included in the API call or the header of a data packet to correlate the wearable device 180 with a particular user. The identifier can be a user identifier (ID) that is assigned to the wearable device 180 when the user registers the wearable device with a health monitoring service, or the identifier can be a network address, such as a media access control (MAC) address or an IP address of the wearable device 180. In some examples, the API 112 can use the identifier to allocate a task ID with the monitored parameter data such that the AI engine 114 or any other process that accesses the data cannot directly correlate the data with a particular user, user account, or user ID. In some cases, the monitored parameter data is also encrypted, either by the wearable device 180 or by the API 112.

In other examples, the API 112 stores the monitored parameter data in a memory or database, and sends a request message to the AI engine 114 that indicates the monitored parameter data is available at the memory or the database. It will be appreciated that the API 112 facilitates the collection of monitored parameter data from one or more wearable devices 180 associated with one or more distinct users or user accounts and provides the AI engine 114 with the monitored parameter data for processing.

In some examples, the AI engine 114 is configured to process inputs with one or more AI algorithms. The AI algorithms can include, but are not limited to, a multi-layer perceptron (MLP) algorithm, a regression model (e.g., a logistic regression model), a random forest model, a gradient boosting machine (GBM) model, a convolution neural network (CNN), a recurrent neural network (RNN), or ensemble models including two or more of the aforementioned AI algorithms. The AI algorithm uses the monitored parameter data to generate outputs that represent predictions related to the health of a user. In some examples, the AI algorithms can be improved by augmenting the monitored parameter data collected by the wearable device with additional information related to the user. In some cases, the additional information is processed to generate embedding data for the user.

In an example, the AI engine 114, upon receiving the monitored parameter data from the API 112, generates a request that is transmitted to the embedding engine 116. The request can include an identifier associated with the wearable device 180. The embedding engine 116 is configured to collect health records or other information from one or more data stores such as a database 160. For example, a health insurance provider can receive claims data from a variety of health care providers. The claims data is stored in a database 160 and used to process insurance claims. However, the embedding engine 116 can query the database 160 for any health records related to a user using the identifier included in the request. Thus, the embedding engine 116 collects additional information from one or more sources that is not available to the wearable device 180.

In some examples, the embedding engine 116 is configured to collect the additional information that is combined with the monitored parameter data from the wearable device 180 to increase the information provided as an input to the AI algorithm. In one example, a health insurance provider receives data related to a user's health as well as general demographic information and/or social determinants information. The data can include claims records received from a health provider, prescription records received from a pharmacy, or laboratory results received from a laboratory or other health care provider. The claims information may contain information about specific medical procedures undergone by the user in the past. The laboratory results can contain detailed information related to a user's comprehensive metabolic panels, for example. The prescription records can include information about the types of medications taken by a user. All of this information can provide a more comprehensive picture of the user's health condition than could be provided by the monitored parameter data alone.

In an example, the embedding engine 116 is configured to process health records for a user via a natural language processing algorithm. Again, the health records correspond to a registered user of the wearable device. It will be appreciated that the health records that are retrieved from the database 160 can have a variety of formats. For example, a claims record may include a set of fields, each field including different information such as a member identifier, insurance product information, medical codes (e.g., ICD9 diagnostic codes), and the like. The job of the embedding engine 116 is to take a number of different natural language or standardized format health records and generate a vector of dimensionless features (e.g., 100 features) that indicates a user's health history over a specified time period. For example, a particular dimension can represent a particular combination of medical codes found throughout the user's health records. This feature vector, generated by a natural language processing algorithm such as Word2vec described in Mikolov et al., "Efficient Estimation of Word Representations in Vector Space," ICLR Workshop Papers, 2013, which is herein incorporated by reference in its entirety, or the like, represents the additional data that is combined with the monitored parameter data.

For example, a member's health history includes a sequence of medical codes including ICD (International Statistical Classification of Diseases) 9/10 diagnostic codes, CPT (Current Procedural Terminology) procedure codes, GPI (Generic Product Identifier) drug codes, and LOINC (Logical Observation Identifiers Names and Codes) lab codes. The embedding engine 116 includes a 100-dimensional lookup matrix that is trained based on health histories of millions of members collected over a number of years. The health history of a particular member can be parsed to extract the codes set forth above, to generate a list of codes included in that member's health history. Each code is then processed by the lookup matrix to generate a corresponding 100-dimensional vector and the average of the vectors for the set of codes generated from the member's health history is provided as the embedding data.

In some examples, the embedding data is combined with additional data such as demographic data (e.g., age, race, gender, etc.) or social determinants data, described in more detail below. When combined with the monitored parameter data, this information provides a more comprehensive view of the user's health that can be processed by the AI algorithm.

The AI engine 114 processes the input vector via one or more AI algorithms. In some examples, the AI engine 114 can generate separate input vectors for each AI algorithm, according to the requirements of the AI algorithm. The output vector from each of the one or more AI algorithms can represent classifiers. A classifier can be a scalar value between 0 and 1 that represents a probability that the user is associated with a particular classification.

In an example, the notification engine 118 can generate a notification message that is transmitted to the wearable device 180 to provide a user of the wearable device with a suggested action. For example, the suggested action can include information to facilitate scheduling an appointment with a healthcare provider. In another example, the notification message is transmitted to a healthcare provider to suggest treatment options that may be applicable to a patient (e.g., the user).

Figure 1B:
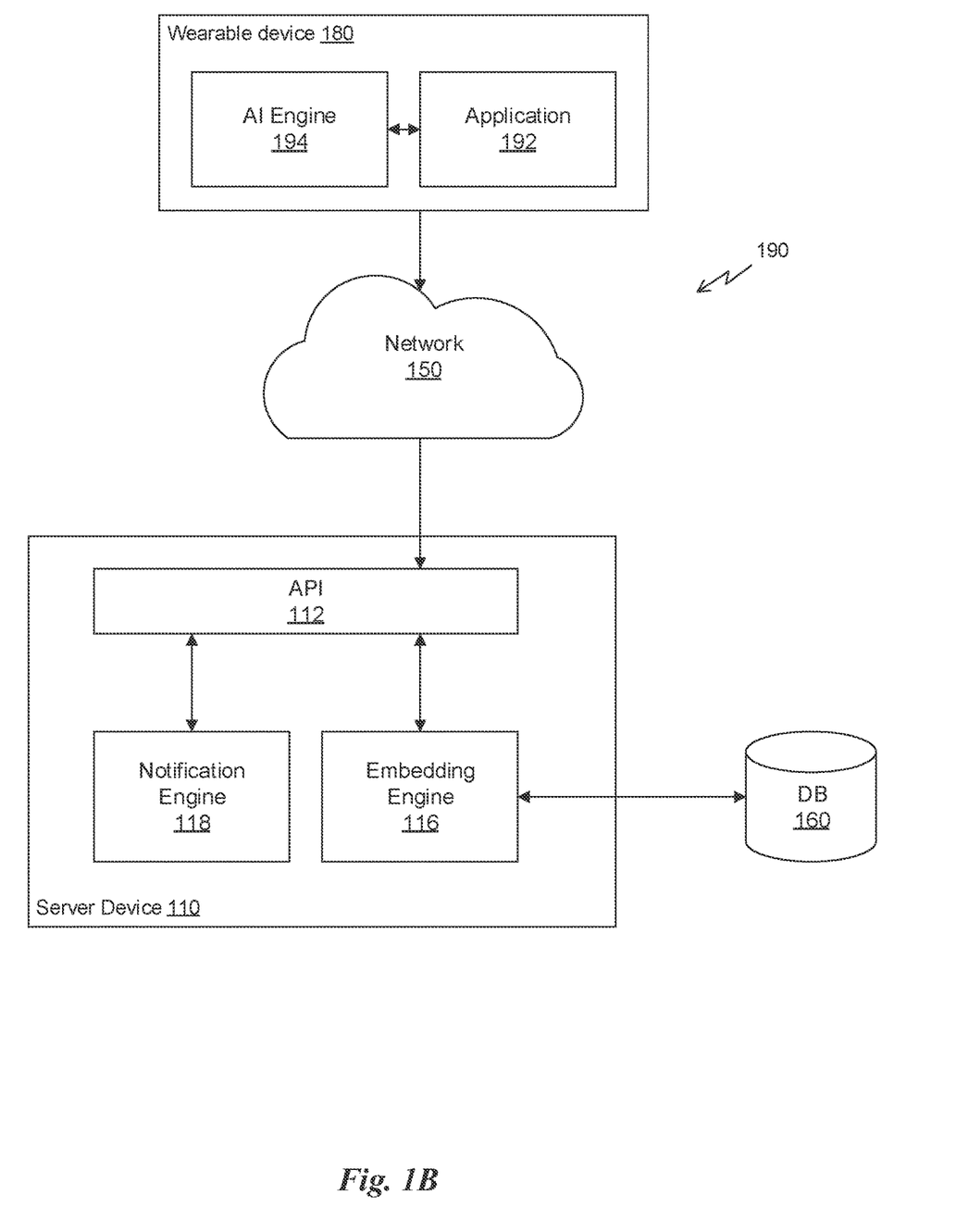
FIG. 1B illustrates a system for monitoring health conditions, in accordance with other examples.

FIG. 1B illustrates a system 100 for monitoring health conditions, in accordance with other examples. As depicted in FIG. 1B, the wearable device 180 includes an application 192 configured to collect data points on one or more parameters monitored by the wearable device 180. In addition, the wearable device 180 also includes the AI engine 194, which is similar to AI engine 114 but is executed locally on the wearable device 180. Rather than transmitting the parameter data collected by the wearable device 180 to the server device 110, the application 192 can request the server device 110 to transmit embedding data generated by the embedding engine 116 to the application 192, which combines the embedding data with the monitored parameter data stored on the wearable device 180. The combined data is then processed by the AI engine 114 to generate the output vector(s) as described above.

It will be appreciated that the system 190 may be more secure than the system 100 as the monitored parameter data is not transmitted over the network 150, and the embedding data transmitted over the network 150 is merely a vector that represents a user's health history and is not easily translated into the original health history information stored in the database 160. However, the system 190 may require more computing capacity in the wearable device 180 in order to execute the AI algorithm(s).

In some examples, the functionality of the wearable device 180 can be split between a wearable activity tracker with limited processing capacity and a mobile device, such as a cellular phone or tablet computer. The mobile device can be connected to the network 150 and the wearable activity tracker can be connected to the mobile device. An application on the mobile device collects monitored parameter data from the wearable activity tracker and transmits the monitored parameter data to the server device 110 to be processed by the AI engine 114, as in system 100, or receives embedding data from the server device 110 to be processed by the AI engine 194, as in system 190. In other examples, the mobile device can be used to provide the wearable device 180 with at least some monitored parameter data. For example, a user can use the mobile device to provide manually logged data related to one or more monitored parameters that are sent to the wearable activity tracker for processing. In such examples, the mobile device can provide additional user interfaces for the wearable activity tracker, but the wearable activity tracker maintains the functionality for processing the monitored parameter data.

Figure 2A:
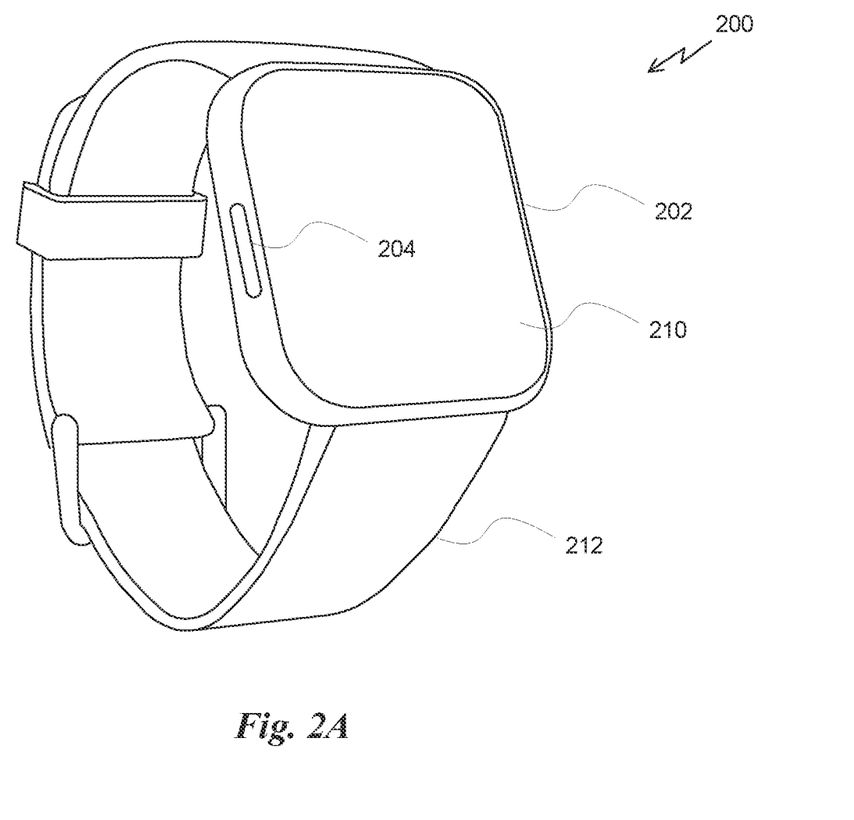
FIGS. 2A & 2B illustrate a wearable device, in accordance with some examples.
Figure 2B:
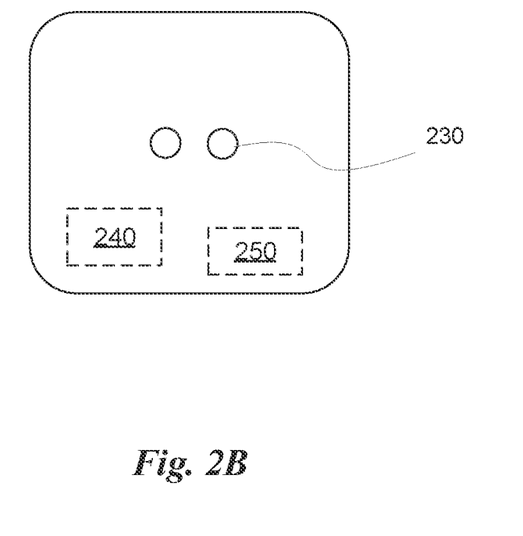

FIGS. 2A & 2B illustrate a wearable device 200, in accordance with some examples. The wearable device 200 is a watch that includes sensors for collecting data points on one or more parameters related to the health of a user. As shown in FIG. 2A, the wearable device 200 includes a body 202 that houses electronics including a processor, a memory, a transceiver, an antenna, a battery, and the like. The wearable device 200 also includes a button 204, a display 210, and a band 212. The display 210 is a liquid crystal display (LCD), an organic light emitting diode (OLED) display, or the like. The display 210 is configured to display information to a user and can include a touch function that enables the user to enter information using the wearable device 200. The display 210 can display information such as a time or date, notifications such as alarms or indications of a text message or phone call, and information related to collected information such as a number of steps counted in a day using a pedometer function or a current heart rate of the user, among other information.

As shown in FIG. 2B, the back of the body 202 can include sensors 230 for collecting monitored parameter data. For example, the sensors 230 can include a light emitting diode that produces a light and a light sensor that detects lights (e.g., optical pulse sensors). The light emitted from the light emitting diode can enter the user's skin and the signal detected by the light sensor can be used to monitor, for example, a user's heart rate or blood oxygen level. The sensors 230 can include other types of sensors such as capacitive sensors, moisture sensors, image sensors, electrooculogram (EOG) or electroretinogram (ERG) sensors, respiration sensors, airflow sensors, temperature sensors, and the like. The scope of the present disclosure is not limited to a specific type of sensor and any sensor capable of collecting any kind of health information about a user is contemplated as being included in the wearable device 200.

As depicted in FIG. 2B, the wearable device 200 includes a processor 240 and a transceiver 250. In some examples, the processor 240 is a system on chip (SoC) and is configured to execute one or more processes that collect monitored parameter data using the sensors 230 and transmit the monitored parameter data to the server device 110 via the transceiver 250. In one example, the wearable device 200 is configured to transmit the monitored parameter data to an access point connected to a network using Wi-Fi or some other wireless technology.

It will be appreciated that the wearable device 200 shown in FIGS. 2A & 2B is only one exemplary device and that other types of wearable devices are contemplated as being within the scope of this disclosure. For example, the wearable device 200 could be a clinical medical device such as a blood glucose monitor or a wearable electrocardiogram (ECG) monitor, smart glasses that include augmented reality and/or virtual reality capabilities, smart rings, bracelets, headbands, headphones, hearing aids, or any other devices worn by a user that include one or more sensors for monitoring some parameter related to the user. In some examples, the wearable device is a smart phone that includes a fitness application that tracks, e.g., an activity level of a user.

Figure 3:
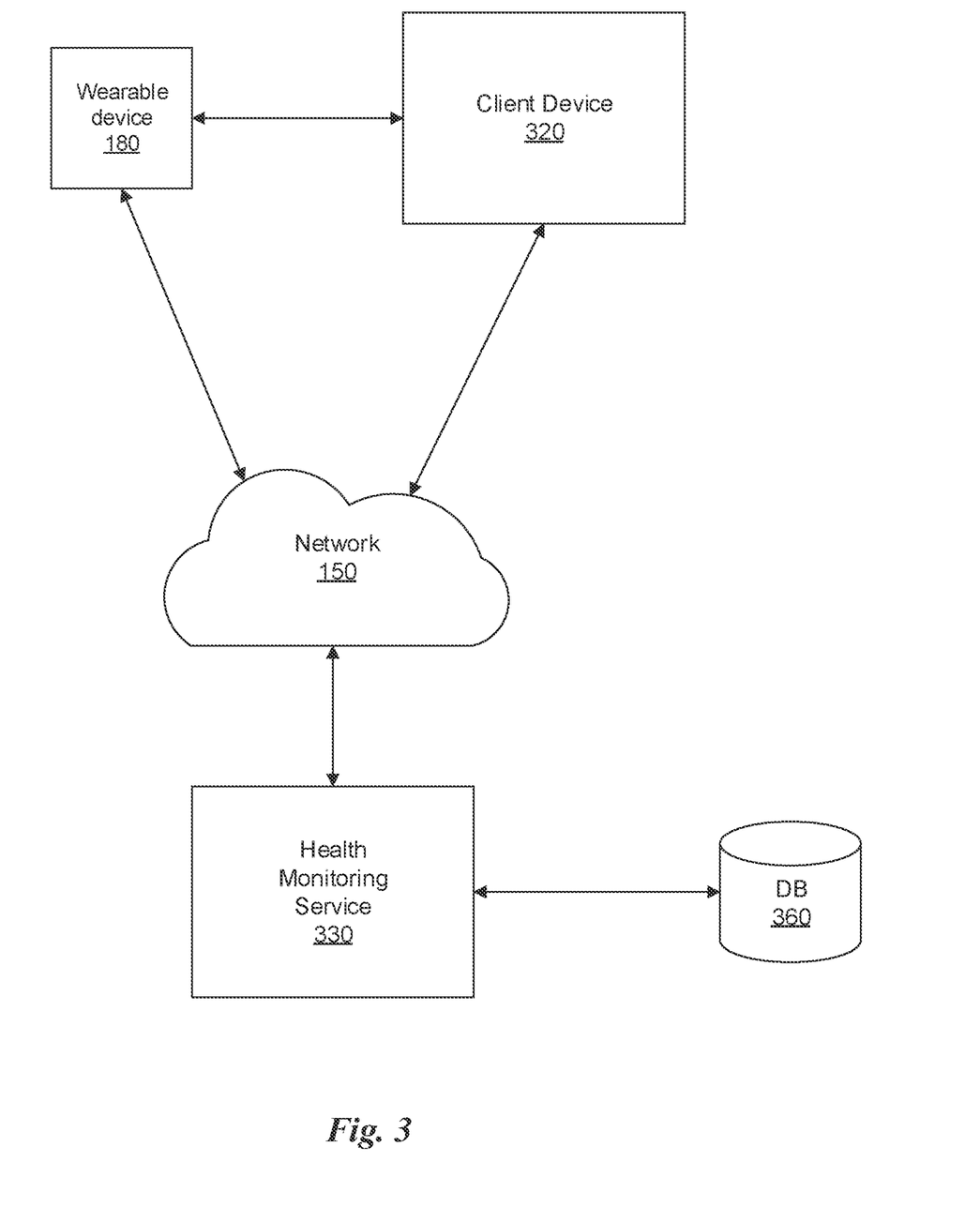
FIG. 3 is a conceptual illustration of a health monitoring service, in accordance with some examples

FIG. 3 is a conceptual illustration of a health monitoring service 330, in accordance with some examples. When a user obtains a wearable device 180, the user can opt-in to use a health monitoring service 330 offered by a service provider. In an example, the user, through a client device 310, can access a web page using a web browser or other application executed by the client device 310. In an example, the web page is a portal for an insurance provider and the user is prompted to log into a user account using credentials established by the user for a user account. Once logged in, the user may select an option provided through the web page to register a wearable device with the account and opt-in to a health monitoring service 330.

In one example, the user provides information to identify the wearable device to the health monitoring service 330. For example, the user can enter a MAC address of the wearable device in a form element provided on the webpage. In another example, the health monitoring service 330 can prompt the user to download an application on the wearable device, where the application is configured to communicate directly with the health monitoring service 330. Once the application is running on the wearable device 330, the user can enter credentials for the user account in the application on the wearable device 180 or, alternatively, the user can be provided with a temporary code at the client device 310, which the user can then enter in the application on the wearable device 180. The temporary code is then transmitted from the wearable device 180 to the health monitoring service 330, which can then associate an identifier corresponding to the wearable device 180 with the user account based on the temporary code.

The examples described above are merely a few of the many possible ways to register the wearable device 180 to the user account for the user. Any means for registering the wearable device 180 to the user account is contemplated as being within the scope of the present disclosure. Once the wearable device 180 is registered to the user account, such as by mapping a user account identifier to an identifier for the wearable device 180 in a database 360, the monitored parameter data received from the wearable device 180 can be associated with health records, or embedding data associated with the health records, corresponding to the user account.

Figure 4:
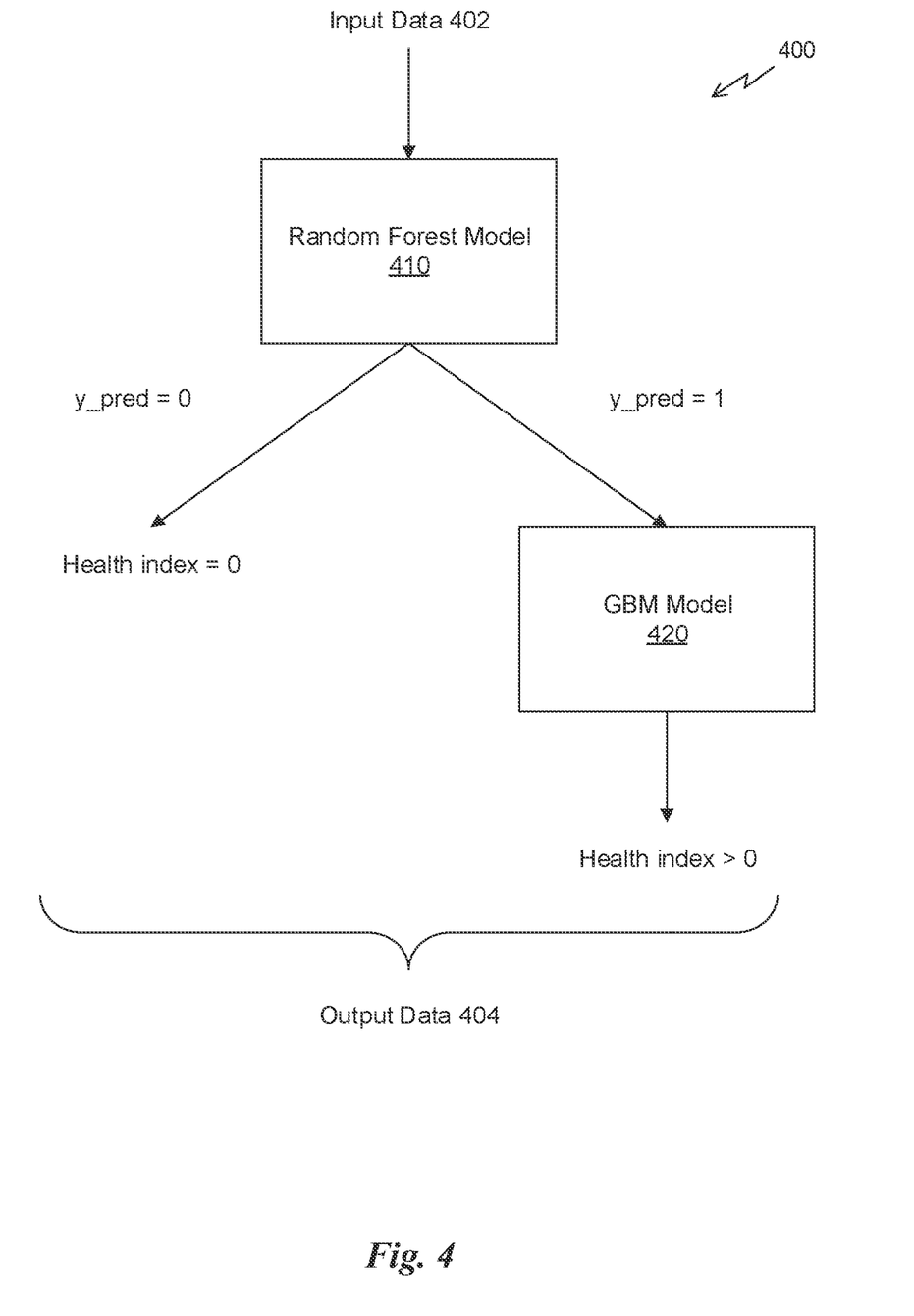
FIG. 4 illustrates a framework used to predict health outcomes, in accordance with some examples

FIG. 4 illustrates a framework 400 used to predict health outcomes, in accordance with some examples. The framework 400 includes one or more AI algorithms designed to predict a health index value for a user. The health index for a user can represent a likelihood that the user will have a total health expenditure above a threshold amount over some time frame (e.g., 90 days). For example, the health index can indicate the likelihood that a user is likely to incur more than $5,000 of health related expenses in the next 90 days, such as through health services such as emergency room visits, prescription costs, and/or surgical procedures. In other examples, the health index can simply refer to a risk associated with the user as to having one or more adverse health outcomes and not necessarily an expenditure amount in monetary terms. The value of the health index can represent the likelihood and/or severity of the near-term adverse health outcome. In general, a lower health index represents a positive health outcome and a higher health index represents a negative health outcome. In other examples, the lower the health index, the more likely the occurrence of an adverse health event.

In an example, the AI algorithm(s) included in the framework 400 can be implemented by the AI engine 114 or AI engine 194 in the systems 100/190. Generally, the framework 400 combines multiple machine learning (ML) models to predict the health index value for a user. As depicted in FIG. 4, the framework 400 includes a random forest model 410, and a gradient boosting machine (GBM) model 420. The random forest model 410 processes the input data 402 with a plurality of decision trees, where each tree classifies whether the input data 402 is likely to be associated with a positive health outcome or a negative health outcome within a given time frame. More particularly, the positive health outcome can represent a prediction that the user will have expenditures equal to or below a threshold value within the next 30, 90, of 120 days, for example. The threshold can be positive (e.g., $500) or zero (i.e., no heath expenditures). The output of the random forest model 410 is based on which classification is predicted by the most decision trees. In one example, the output of the random forest model 410 is used to divide a plurality of users into two subsets of users: a first subset predicted to have positive health outcomes and a second subset predicted to have negative health outcomes.

In one example, the input data 402 includes monitored parameter data and embedding data corresponding to a particular user. The embedding data can be generated by analyzing health records for the user, as discussed in more detail above. In some examples, the input data can be augmented with demographic data, social determinants data, and the like in addition to the monitored parameter data and the embedding data.

It will be appreciated that not every user may be associated with a full set of input data 402. For example, some users may not track health characteristics with a wearable device or have chosen not to opt-in to the health monitoring service 330. In other cases, some users may have an incomplete or blank claims history, especially when the users are not currently or have only recently become members of a health plan offered by a plan provider (i.e., insurance provider). In such cases, a portion of (or all) the input data 402 may be imputed to the user based on one or more other users that are similar to the user. For example, if a user has been a plan member for less than 6 months, the claims history of the user may be too new to be an accurate predictor of the user's health history. In such cases, other data, such as demographic data, social determinants data, and/or monitored parameter data may be used to determine imputed values attributed to the user based on average values for these features for a plurality of similar users selected based on the demographic data, social determinants data, and/or monitored parameter data. For example, a 32 year old, white male living in an urban environment may be assigned imputed values for embedding data averaged from embedding data for a subset of other white males aged 30-34 living in urban environments. In other examples, the input data 402 may be left sparse (i.e., incomplete) and the random forest model 410 can be trained based on both complete and incomplete data sets.

Given that the first subset of users are predicted to have positive outcomes (e.g., likely to have zero health expenditures over the next 90 days, for example), this set of users is not processed by the GBM model 420, and these users are assigned a minimum health index value (e.g., health index=0). However, the second subset of users may be processed by the GBM model 420 in order to predict a magnitude of the users' negative health outcomes and, thereby, generate a corresponding health index value (e.g., between 0 and 1). For example, the GBM model 420 may be trained to predict a total health expenditure for each user in the second subset of users, and map the total health expenditure to the corresponding health index value. In other examples, the GBM model 420 can be trained to predict the health index value directly and/or the health index can be assigned a value equal to the total health expenditure (e.g., between 0 and 15,000, capped).

It will be appreciated that some users may experience some health expenditures due to chronic conditions that may be rather modest, such as requiring an ongoing generic prescription to be filled or visiting a specialist once every six months. However, other users may experience vastly more expensive, predictable or unpredictable health expenditures, such as those caused by an unexpected injury or traumatic event such as a car accident or a cancer diagnosis that requires chemotherapy or surgery.

In an example, the second subset of users can be further processed by the GBM model 420 to predict the users' total health expenditure, combining both medical and prescription costs over a particular time frame such as the next 90 days. In an example, the GBM model 420 is an implementation of the Extreme Gradient Boost (XGBoost) algorithm, which is described in more detail in Chen et al., "XGBoost: A Scalable Tree Boosting System," arXiv:1603.02754v3, Jun. 10, 2016, the contents of which are incorporated herein in its entirety.

The output of the framework 400, i.e., the health index for each user, can then be used by the notification engine 118 to determine whether to send a message to the user or personnel associated with providing health care to the user to attempt to intervene and reduce the future health expenditures by early intervention. In one example, the notification engine 118 compares the value for the health index to a threshold (e.g., 0.5) and, if the value for the health index is above the threshold, then the notification engine 118 sends a notification message to the wearable device, the client device 320 (e.g., a mobile phone), and/or a computer system associated with a healthcare provider, pharmacy, or other personnel associated with providing health care to the user.

In some examples, the user may opt-in to receive notification messages. The notification engine 118 may be prevented from sending the notification message unless the user has opted in to receive notification messages. In some examples, the notification engine 118 can be connected to a database that maps a user account for the user with a particular treatment facility or facilities that the user has used in the past. For example, the user account may be connected to a primary care physician's (PCP) office, a pharmacy, an urgent care clinic, or the like. The notification engine 118 can retrieve information about one or more treatment facilities and include the information in the notification message. For example, the notification message can include a link to a PCP website or a phone number for the PCP office along with a reminder to schedule a visit to see the user's PCP if they are experiencing any symptoms.

Furthermore, each of the models shown in FIG. 4 can be trained using historical monitored parameter data and claims data to generate a training data set. For example, claims data and/or monitored parameter data can be analyzed for specific time windows and total health expenditures for a subsequent time period (e.g., 90 days) after the window can be calculated for each user. The calculated expenditure can then be used to assign each window of claims data and/or monitored parameter data a ground-truth health index value. This training data set can then be used to train the random forest model 410 and/or the GBM model 420 using known training techniques such as gradient descent with back propagation.

Figure 5:
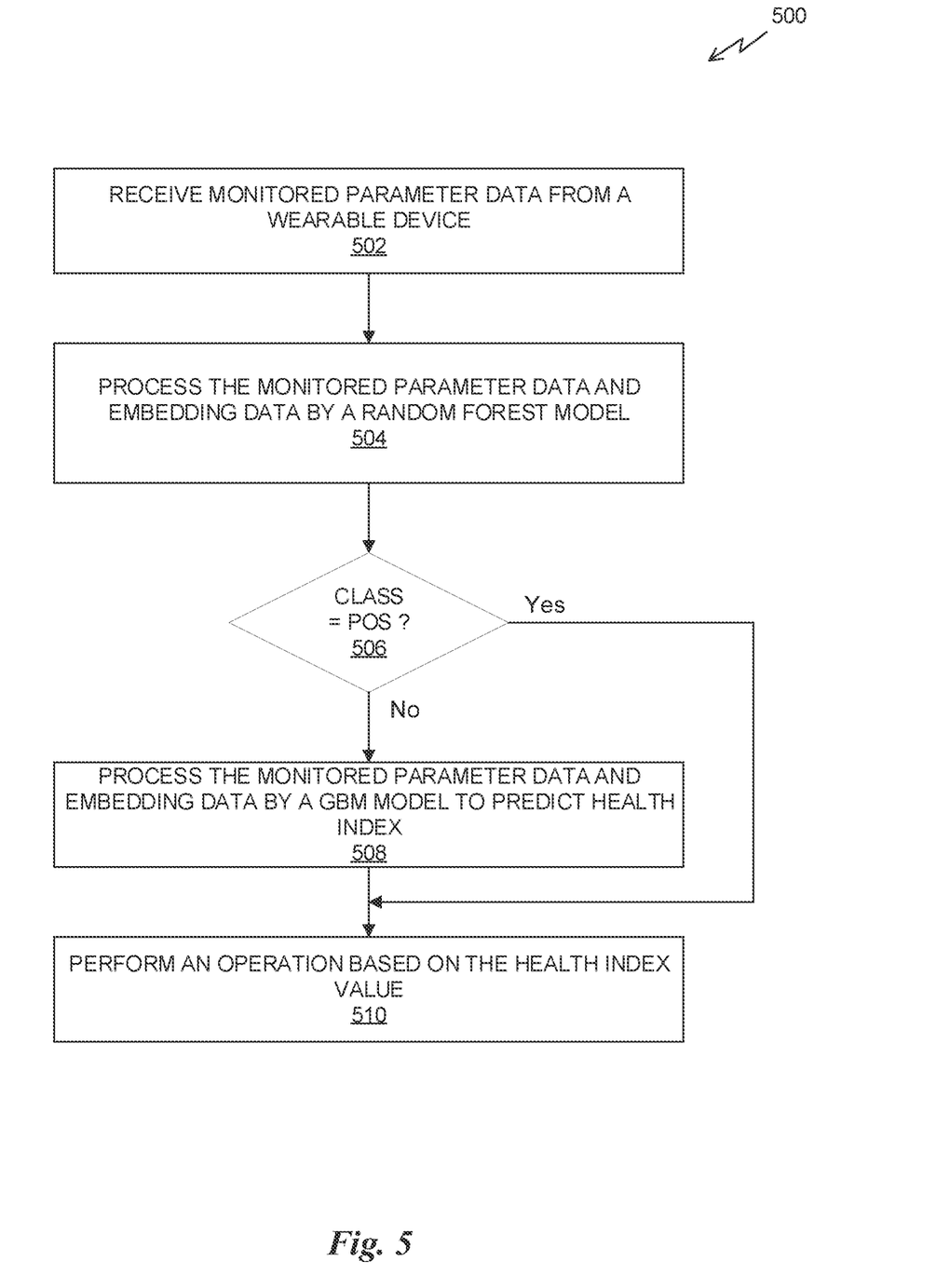
FIG. 5 is a flow diagram of a method for predicting health outcomes, in accordance with some examples.

FIG. 5 is a flow diagram of a method 500 for predicting health outcomes, in accordance with some examples. The method 500 can be performed by a program, custom circuitry, or by a combination of custom circuitry and a program. Furthermore, persons of ordinary skill in the art will understand that any system that performs method 500 is within the scope and spirit of the examples described herein.

At step 502, monitored parameter data and embedding data are received for a user. In an example, a server device 110 receives the monitored parameter data from a wearable device 180 via a network 150. The monitored parameter data can include data points (e.g., samples) for one or more monitored parameters that can include at least one of: a heart rate; an oxygen level, an activity level including at least one of a number of steps, a number of flights climbed, or a duration of exercise, or a number of calories burned. In another example, the wearable device 180 collects the monitored parameter data and receives the embedding data from a server device 110.

In some examples, the monitored parameter data can be imputed to a user based on monitored parameter data received from wearable devices of one or more other users. The one or more other users may be a subset of users associated with monitored parameter data that are similar to a user. Similarity can be defined based on the clustering of users (e.g., via k-means or other clustering algorithms) according to embedding data generated from health records.

In one example, the embedding data can be generated by processing health records (e.g., claims data, lab results, etc.) by a natural language processing algorithm that extracts diagnostic codes or other information from the health records to create a vector of dimensionless features (e.g., a vector of 100 features). The embedding data can represent the health history of a user extracted from the health records, and clusters of users having similar embedding data vectors can be identified as similar users in order to impute certain characteristics from monitored parameter data to a user. For example, average values of monitored parameter data from similar cohorts can be imputed to a particular user that lacks monitored parameter data from a wearable device.

In other examples, embedding data can be imputed to a user based on the monitored parameter data and/or other information such as demographics data and/or social determinants data. For example, when a user lacks significant claims history because the user is not a plan member or has only been a plan member for a short time, embedding data from other users that are similar to the user can be imputed to that user. For example, embedding data for users that have similar monitored parameter data to the user can be imputed to the user.

At step 504, the monitored parameter data and the embedding data is processed by a random forest model 410 to classify the user according to one of two classes (i.e., a binary classification). At step 506, the classification of the user is used to determine a manner of assigning a health index value to a user. A first subset of users classified by the random forest model 410 according to a first class (y_pred=0) can be identified as having positive, near-term health outcomes and are assigned a minimum health index value (e.g., health index=0). The GBM model 420 is not used to assign a health index value to users in the first subset of users. In contrast, a second subset of users classified according to a second class (y_pred=1) can be identified as having negative, near-term health outcomes and will be assigned a health index value based on the output of the GBM model 420.

At step 508, the monitored parameter data and the embedding data is processed by a GBM model 420 to predict a health index value for each user of the second subset of users. In particular, for those users classified as predicted to have negative, near-term health outcomes at step 506, the GBM model 420 processes the monitored parameter data and the embedding data to predict a health index value for the user. In one example, the GBM model 420 predicts a health index value for the user between 0 and 1, with values closer to 0 representing lower total health expenditures and values closer to 1 representing higher total health expenditures. In another example, the GBM model 420 predicts a total value of health expenditures in the near term (e.g., next 90 days), and a health index value is calculated by mapping the total value of health expenditures to a value between 0 and 1. In an example, any value of health expenditures over a threshold value (e.g., an expenditure cap), is assigned the maximum health index value of 1. The threshold value may be, for example, $15,000 or any other figure as selected for a particular application.

At step 510, an operation is performed based on the health index value. For example, in one example, the operation may comprise sending a notification to the user, via the wearable device 180 and/or client device 320, when the health index value is above a threshold value. A high health index value can indicate a high likelihood that the user is likely to expend significant dollars in the near term for health services. By notifying the user and attempting to get the user to see a primary care physician and/or participate in healthier lifestyle options such as walking more or going to the gym, the total expenditures may potentially be reduced, saving the user and the insurance provider costs and allowing premiums for insurance products to remain lower for the total insured population. In addition, encouraging early intervention by encouraging more wellness visits to a PCP may potentially reduce the use of higher cost emergency services.

In an example, the notification is sent from a server device to a health application on a client device. The notification can cause the application to modify one or more features or characteristics of the application. For example, the notification can cause activity goals to be adjusted (such as increasing the number of daily steps or a calorie count in an activity goal of the user), refine a point allocation (e.g., awarding more or less points associated with different incentivized behavior), and so forth.

As another example, in accordance with other examples, the operation may comprise generating an invoice. Commonly, an insurance plan may offer discounts or rebates based on users participating in healthy lifestyle initiatives such as joining a gym or using a pedometer to record a minimum number of steps per day. As an alternative, the insurance provider may offer certain discounts to users who have a health index below a certain threshold. An invoice processing system may utilize the framework 400 to calculate each user's health index value and automatically apply a discount or rebate to a user's invoice based on a low health index value indicating a low likelihood of a negative health outcome in the near term. Such rebates may be used to incentivize use of the wearable activity trackers and/or encourage behaviors that promote a healthy lifestyle.

As yet another example, the insurance provider can use the health index value to drive certain marketing activities. For example, certain users can be grouped (e.g., via a clustering algorithm such as k-means or others) according to similar health index values, and these groups of users can be divided into two or more sub-groups of similar cohorts in order to study the efficiency of certain customer engagement activities. For example, a group of similar cohorts can be separated into two sub-groups: notifications are sent to the first sub-group encouraging these users to get 10,000 steps a day, and no notifications are sent to the second sub-group. The total health expenditures for the two groups can then be tracked for the next 90 days to determine if this type of engagement is effective at reducing negative health outcomes. This can sometimes be referred to as A/B testing. In this manner, various engagement activities or promotional incentives can be tested to determine which types of incentives or engagement activities are most effective at promoting a healthy lifestyle and/or improving the health outcomes of the plan members.

In an example, a notification could be sent to a third-party associated with the user, such as a primary care physician, pharmacy registered to the user, or other personnel involved in the health care of the user. The user may be required to opt-in to have notifications sent to the third-party. By sharing a notification that indicates recommended interventions for the user with the third-party involved in the user's health care, the third-party may be more likely to help encourage the user to participate in the recommended interventions.

Figure 6:
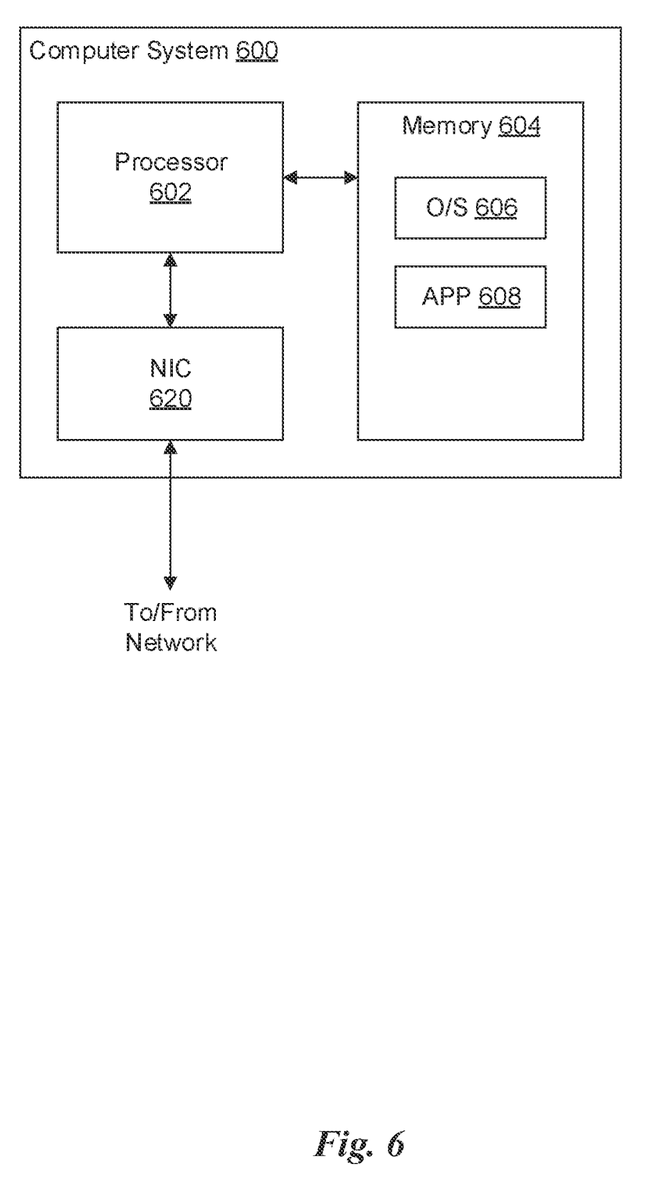
FIG. 6 illustrates an exemplary computer system, in accordance with some examples.

FIG. 6 illustrates an exemplary computer system 600, in accordance with some examples. The computer system 600 includes a processor 602, a non-volatile memory 604, and a network interface controller (NIC) 620. The processor 602 can execute instructions that cause the computer system 600 to implement the functionality various elements of the system 100 described above. For example, the wearable device 180 and/or the server device 110 can each take the form of the computer system 600.

Each of the components 602, 604, and 620 can be interconnected, for example, using a system bus to enable communications between the components. The processor 602 is capable of processing instructions for execution within the system 600. The processor 602 can be a single-threaded processor, a multi-threaded processor, a vector processor or parallel processor that implements a single-instruction, multiple data (SIMD) architecture, or the like. The processor 602 is capable of processing instructions stored in the volatile memory 604. In some examples, the volatile memory 604 is a dynamic random access memory (DRAM). The instructions can be loaded into the volatile memory 604 from a non-volatile storage, such as a Hard Disk Drive (HDD) or a solid state drive (not explicitly shown), or received via the network. In an example, the volatile memory 604 can include instructions for an operating system 606 as well as one or more applications 608. It will be appreciated that the application(s) can be configured to provide the functionality of one or more components of the system 100, as described above. The NIC 620 enables the computer system 600 to communicate with other devices over a network, including a local area network (LAN) or a wide area network (WAN) such as the Internet.

It will be appreciated that the computer system 600 is merely one exemplary computer architecture and that the processing devices implemented in the system 100 can include various modifications such as additional components in lieu of or in addition to the components shown in FIG. 6. For example, in some examples, the computer system 600 can be implemented as a system-on-chip (SoC) that includes a primary integrated circuit die containing one or more CPU cores, one or more GPU cores, a memory management unit, analog domain logic and the like coupled to a volatile memory such as one or more SDRAM integrated circuit dies stacked on top of the primary integrated circuit dies and connected via wire bonds, micro ball arrays, and the like in a single package (e.g., chip). In another example, the computer system 600 can be implemented as a server device, which can, in some examples, execute a hypervisor and one or more virtual machines that share the hardware resources of the server device.

It is noted that the techniques described herein may be embodied in executable instructions stored in a computer readable medium for use by or in connection with a processor-based instruction execution machine, system, apparatus, or device. It will be appreciated by those skilled in the art that, for some examples, various types of computer-readable media can be included for storing data. As used herein, a "computer-readable medium" includes one or more of any suitable media for storing the executable instructions of a computer program such that the instruction execution machine, system, apparatus, or device may read (or fetch) the instructions from the computer-readable medium and execute the instructions for carrying out the described examples. Suitable storage formats include one or more of an electronic, magnetic, optical, and electromagnetic format. A non-exhaustive list of conventional exemplary computer-readable medium includes: a portable computer diskette; a random-access memory (RAM); a read-only memory (ROM); an erasable programmable read only memory (EPROM); a flash memory device; and optical storage devices, including a portable compact disc (CD), a portable digital video disc (DVD), and the like.

It should be understood that the arrangement of components illustrated in the attached Figures are for illustrative purposes and that other arrangements are possible. For example, one or more of the elements described herein may be realized, in whole or in part, as an electronic hardware component. Other elements may be implemented in software, hardware, or a combination of software and hardware. Moreover, some or all of these other elements may be combined, some may be omitted altogether, and additional components may be added while still achieving the functionality described herein. Thus, the subject matter described herein may be embodied in many different variations, and all such variations are contemplated to be within the scope of the claims.

To facilitate an understanding of the subject matter described herein, many aspects are described in terms of sequences of actions. It will be recognized by those skilled in the art that the various actions may be performed by specialized circuits or circuitry, by program instructions being executed by one or more processors, or by a combination of both. The description herein of any sequence of actions is not intended to imply that the specific order described for performing that sequence must be followed. All methods described herein may be performed in any suitable order unless otherwise indicated herein or otherwise clearly contradicted by context.

The use of the terms "a" and "an" and "the" and similar references in the context of describing the subject matter (particularly in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. Furthermore, the foregoing description is for the purpose of illustration only, and not for the purpose of limitation, as the scope of protection sought is defined by the claims as set forth hereinafter together with any equivalents thereof. The use of any and all examples, or exemplary language (e.g., "such as") provided herein, is intended merely to better illustrate the subject matter and does not pose a limitation on the scope of the subject matter unless otherwise claimed. The use of the term "based on" and other like phrases indicating a condition for bringing about a result, both in the claims and in the written description, is not intended to foreclose any other conditions that bring about that result. No language in the specification should be construed as indicating any non-claimed element as essential to the practice of the examples as claimed.

What is claimed is:

1. A system for predicting health outcomes, the system comprising:
   a memory storing instructions; and
   one or more processors that, responsive to executing the instructions, are configured to:
      receive monitored parameter data from a wearable device;
      obtain embedding data corresponding to a user registered to the wearable device;
      process the monitored parameter data and the embedding data by a random forest model comprising a plurality of decision trees to generate a binary classification of the user, wherein each of the plurality of decision trees generates a decision tree classification based on the monitored parameter data and the embedding data, wherein the binary classification is a first classification based on a majority of the decision tree classifications being the first classification, and wherein the binary classification is a second classification based on a majority of the decision tree classifications being the second classification;
      based on the user being classified according to the first classification, process the monitored parameter data and the embedding data by a gradient boosting machine (GBM) model to generate an index value indicating a health of the user that is registered to the wearable device;
      based on the user being classified according to the second classification, assign the index value a minimum index value; and
      perform an operation based on the index value.

2. The system of claim 1, wherein the wearable device is an activity tracker, and wherein the monitored parameter data comprises information logged by the user manually and data points related to one or more of:
   a heart rate;
   an oxygen level;
   an activity level comprising at least one of a number of steps, a number of flights climbed, or a duration of exercise; or
   a number of calories burned.

3. The system of claim 1, wherein obtaining the embedding data comprises processing health records for a user via a natural language processing algorithm, wherein the health records correspond to the user registered to the wearable device.

4. The system of claim 3, wherein the health records are stored in a database and comprise at least one of:
   claims records received from a health care provider;
   prescription records received from a pharmacy; or
   laboratory results received from a laboratory or other health care provider.

5. The system of claim 1, wherein the operation comprises sending a notification message to at least one of the wearable device or a client device associated with the wearable device.

6. The system of claim 5, wherein the notification message is transmitted responsive to determining that the index value is above a threshold value to provide the user of the wearable device with a suggested action, wherein the suggested action comprises information to facilitate scheduling an appointment with a healthcare provider.

7. The system of claim 1, wherein the operation comprises generating an invoice for the user, wherein the invoice is adjusted based on the index value.

8. The system of claim 1, wherein the operation comprises dividing a plurality of users similar to the user into at least two groups, wherein similarity of the users is determined based on the index value for each user in the plurality of users, and taking a first action with respect to a first group of users in the at least two groups and taking a second action, different from the first action, with respect to a second group of users in the at least two groups.

9. A method for predicting health outcomes, the method comprising:
   receiving monitored parameter data from a wearable device;
   obtaining embedding data corresponding to a user registered to the wearable device;
   processing the monitored parameter data and the embedding data by a random forest model comprising a plurality of decision trees to generate a binary classification of the user, wherein each of the plurality of decision trees generates a decision tree classification based on the monitored parameter data and the embedding data, wherein the binary classification is a first classification based on a majority of the decision tree classifications being the first classification, and wherein the binary classification is a second classification based on a majority of the decision tree classifications being the second classification;
   based on the user being classified according to the first classification, processing the monitored parameter data and the embedding data by a gradient boosting machine (GBM) model to generate an index value indicating a health of the user that is registered to the wearable device;
   based on the user being classified according to the second classification, assigning the index value a minimum index value; and performing an operation based on the index value.

10. The method of claim 9, wherein the wearable device is an activity tracker, and wherein the monitored parameter data comprises information logged by the user manually and data points related to one or more of:
   a heart rate;
   an oxygen level;
   an activity level comprising at least one of a number of steps, a number of flights climbed, or a duration of exercise; or
   a number of calories burned.

11. The method of claim 10, wherein obtaining the embedding data comprises processing health records for a user via a natural language processing algorithm, wherein the health records correspond to the user registered to the wearable device.

12. The method of claim 11, wherein the health records are stored in a database and comprise at least one of:
   claims records received from a health provider;
   prescription records received from a pharmacy; or
   laboratory results received from a laboratory or other health care provider.

13. The method of claim 9, wherein the operation comprises sending a notification message to at least one of the wearable device or a client device associated with the wearable device.

14. The method of claim 13, wherein the notification message is transmitted responsive to determining that the index value is above a threshold value to provide the user of the wearable device with a suggested action, wherein the suggested action comprises information to facilitate scheduling an appointment with a healthcare provider.

15. The method of claim 9, wherein the operation comprises generating an invoice for the user, wherein the invoice is adjusted based on the index value.

16. The method of claim 9, wherein the index value generated by the GBM is a value between 0 and 1 that indicates predicted health expenditures by the user.

17. The method of claim 9, wherein performing the operation based on the index value comprises:
   based on the index value, generating instructions to modify one or more features or characteristics of an application operating on the wearable device; and
   providing the instructions to the wearable device to direct the wearable device to modify the one or more features or characteristics of the application.

18. The method of claim 17, wherein providing the instructions to the wearable device to direct the wearable device to modify the one or more features or characteristics of the application comprises:
   directing the wearable device to adjust activity goals of the user or to refine a point allocation of the user.

19. The method of claim 9, further comprising:
   receiving user input indicating approval to provide health information to a third-party computing device, and wherein performing the operation based on the index value comprises providing a notification message indicating the health of the user to the third-party computing device based on the user input indicating the approval and the index value.

20. A non-transitory computer readable medium storing instructions that, responsive to execution by one or more processors, cause the one or more processors to:
   receive monitored parameter data from a wearable device;
   obtain embedding data corresponding to a user registered to the wearable device;
   process the monitored parameter data and the embedding data by a random forest model comprising a plurality of decision trees to generate a binary classification of the user, wherein each of the plurality of decision trees generates a decision tree classification based on the monitored parameter data and the embedding data, wherein the binary classification is a first classification based on a majority of the decision tree classifications being the first classification, and wherein the binary classification is a second classification based on a majority of the decision tree classifications being the second classification;
   based on the user being classified according to the first classification, process the monitored parameter data and the embedding data by a gradient boosting machine (GBM) model to generate an index value, or indicating a health of the user that is registered to the wearable device;
   based on the user being classified according to the second classification, assign the index value a minimum index value; and
   perform an operation based on the index value.

* * * * *